United States Patent
Mikkelsen et al.

(10) Patent No.: US 6,600,560 B2
(45) Date of Patent: Jul. 29, 2003

(54) OPTICAL MEASUREMENT ARRANGEMENT HAVING AN ELLIPSOMETER

(75) Inventors: Hakon Mikkelsen, Magdala (DE); Horst Engel, Giessen (DE); Lambert Danner, Wetzlar-Naunheim (DE); Christof Stey, Wetzlar (DE)

(73) Assignee: Leica Microsystems Jena GmbH, Jena (DE)

( * ) Notice: Subject to any disclaimer, the term of this patent is extended or adjusted under 35 U.S.C. 154(b) by 3 days.

(21) Appl. No.: 09/845,763

(22) Filed: May 2, 2001

(65) Prior Publication Data

US 2002/0027657 A1 Mar. 7, 2002

(30) Foreign Application Priority Data

May 2, 2000 (DE) .......................................... 100 21 378

(51) Int. Cl.[7] .................................................. G01J 4/00
(52) U.S. Cl. ..................................................... 356/369
(58) Field of Search ................................. 356/364, 365, 356/366, 367, 368, 369, 370, 600, 601, 609, 612, 613; 250/225

(56) References Cited

U.S. PATENT DOCUMENTS

| | | | |
|---|---|---|---|
| 5,042,951 A | 8/1991 | Gold et al. ................. 356/369 |
| 5,120,966 A | 6/1992 | Kondo ........................ 250/372 |
| 5,596,406 A | 1/1997 | Rosencwaig et al. ....... 356/327 |
| 5,608,526 A | * 3/1997 | Piwonka-Corle et al. ... 356/369 |
| 6,134,011 A | * 10/2000 | Klein et al. ................. 250/225 |
| 6,184,984 B1 | * 2/2001 | Lee et al. .................... 356/369 |
| 6,198,531 B1 | * 3/2001 | Myrick et al. .............. 356/213 |

* cited by examiner

*Primary Examiner*—Tu T. Nguyen
(74) *Attorney, Agent, or Firm*—Foley & Lardner (57) ABSTRACT

The invention concerns an optical measurement arrangement having an ellipsometer, in which an incident beam (16) of polarized light is directed at an angle of incidence $\alpha \neq 0°$ onto a measurement location (M) on the surface of a specimen (P). Information concerning properties of the specimen (P), preferably concerning layer thicknesses and optical material properties such as refractive index n, extinction coefficient k, and the like, is obtained from an analysis of a return beam (17) reflected from the specimen (P). The incident beam (16) is directed by a mirror objective (15) onto the surface of the specimen (P). The return beam (17) is also captured by the mirror objective (15). The result is to create an optical measurement arrangement, operating on the ellipsometric principle, which has a simple, compact configuration and permits a high measurement accuracy down to the sub-nanometer range.

13 Claims, 7 Drawing Sheets

OPTICAL MEASUREMENT ARRANGEMENT HAVING AN ELLIPSOMETER

CROSS REFERENCE TO RELATED APPLICATIONS

This invention claims priority of a German patent application DE 100 21 378.2 which is incorporated by reference herein.

FIELD OF THE INVENTION

The invention concerns an optical measurement arrangement having an ellipsometer, in which an incident beam of polarized light is directed at an angle of incidence a $\alpha \neq 0°$ onto a measurement location on the surface of a specimen, and information concerning properties of the specimen, preferably concerning layer thicknesses, optical material properties such as refractive index n, extinction coefficient k, and the like, is obtained from an analysis of a return beam reflected from the specimen.

BACKGROUND OF THE INVENTION

Optical measurement arrangements that are based on the principle of ellipsometry or spectrophotometry, and their use for layer thickness measurement, are known in many varieties from the existing art. They have been successfully utilized in particular in the measurement of thin layers on the patterns of wafer surfaces. Whereas an oblique incidence of the measurement light onto the specimen is required in ellipsometry, a perpendicular light incidence is preferable in spectrophotometry in order to rule out polarization effects as much as possible. A measurement arrangement operating on the principle of spectrophotometry is known, for example, from U.S. Pat. No. 5,120,966.

Since increasingly fine patterns and thinner layers are desirable in particular in wafer manufacture, requirements are also increasing in terms of the accuracy of the optical measurement arrangements with which the dimensional consistency of the patterns and layers can be verified.

To allow even complex patterns and layer systems to be measured, for reliable results it is usually necessary to apply several measurement principles; the measurement operations should be performed as rapidly in succession as possible at a single point, since positioning (given that measurement location sizes are on the order of micrometers wide) is very laborious.

Existing measurement arrangements require different optical assemblies for different measurement principles. Arrangement and coordination of the assemblies with respect to one another must be accomplished in such a way that the pertinent beam paths do not, if possible, substantially influence each other. In the case of a measurement arrangement for the inspection of wafer surfaces, for example, a measurement objective of a spectrophotometer must be arranged over the measurement location. It is also necessary to guide the laser beam of a focusing device onto the measurement location so that the region of a specimen to be examined can be correctly positioned with respect to the measurement objective. An additional ellipsometer must then be arranged alongside the measurement objective of the spectrophotometer, and the incident beams of the ellipsometer must also strike the measurement location. A corresponding device of the ellipsometer for collecting and analyzing an output beam of light reflected from the specimen must furthermore be arranged alongside the spectrophotometer measurement objective. The configuration of a measurement arrangement of this kind is, however, relatively complex.

U.S. Pat. No. 5,042,951 describes a measurement arrangement in which ellipsometric measurement can be performed with only one objective. Many different angles of incidence can be analyzed simultaneously, and even a small measurement spot (approximately 1 μm or less) can be used. With the arrangement described therein it is not possible, however, simultaneously to analyze several wavelengths separately and spectroscopically.

U.S. Pat. No. 5,596,406 has made improvements over this; it recommends, inter alia, the simultaneous measurement of several wavelengths using a halogen lamp as the illumination source.

The arrangements proposed in U.S. Pat. No. 5,042,951 and in U.S. Pat. No. 5,596,406 consistently use normal dispersive lens optics and glass-plate beam splitters, however, which are suitable for the VIS-IR region but not for the entire UV-VIS-IR region. The reason is the large chromatic aberration of the specimen image, and the decreasing transmission in the deep UV of broadband anti-reflection coatings and broadband reflection coatings.

SUMMARY OF THE INVENTION

In this context, it is the object of the invention to create an optical measurement arrangement, operating on the principle of ellipsometry, which has a simple, compact configuration and allows a high measurement accuracy, down to the sub-nanometer range, over the entire UV-VIS-IR spectral region.

This object is achieved by an optical measurement arrangement of the kind cited initially in which the incident beam is directed by a mirror objective onto the measurement location on the surface of the specimen, and the return beam is also captured by the mirror objective.

The use of a mirror objective for ellipsometry makes it possible to eliminate the separate optical assemblies hitherto used for the purpose. It is furthermore possible to use the mirror objective simultaneously for spectrography, thus reducing the equipment requirement of the optical measurement arrangement to a single measurement instrument, and allowing a particularly space-saving design for the entire measurement arrangement to be realized.

The mirror objective moreover has the advantage, as compared to optics conventionally used in ellipsometry, of being UV-transparent, so that a measurement with light wavelengths in the spectral region from 190 nm to 800 nm can be performed. In the measurement of small layer thicknesses in particular, measurement with short wavelengths in the UV region results in a high measurement accuracy.

The mirror objective further makes it possible to apply an incident beam onto the measurement location on the specimen within an angular range of 18° to 41° from the optical axis of the mirror objective. The relatively high numerical aperture of the objective, i.e. its large angle of incidence range, allows both thin and thick layers to be measured with high accuracy. Because of the relatively high aperture of the mirror objective, microspot sizes of approximately 400 nm to 2 μm are possible.

In an advantageous embodiment of the invention, the light reflected from the specimen is introduced via a light-guiding device into an analysis device, the light-guiding device comprising a plurality of individual light-guiding fibers. A further light-guiding device having a plurality of individual light-guiding fibers is provided in order to convey to the analysis device measurement light that is uninfluenced by the specimen. The use of light-guiding fibers permits the analysis device to be arranged very flexibly with respect to the mirror objective and to an illumination source that is necessarily also present. Connecting the light-guiding devices in parallel makes possible a reduction in the occurrence of noise signals upon analysis, since although the measurement signal arrives in noisy fashion at the receiver, that noise is nevertheless correlated with the noise of the reference light channel, so that it can be effectively compensated for.

A polarizing beam splitter is preferably arranged after the mirror objective, in such a way that the return beam coming from the mirror objective is divided, in the polarizing beam splitter, into two s- and p-polarized output beams which are conveyed separately to the analysis device. It is thereby possible to analyze the polarization state of the light reflected from the specimen. The beam splitter can be a Wollaston analyzer or a Rochon analyzer. The Wollaston prism has the advantage over the Rochon prism that the separation angle between the respectively s- and p-polarized output beams is greater.

A focusing lens is preferably arranged between the exit of the polarizing beam splitter and the light-guiding device that is configured in two-channel fashion, in order to focus the s- and p-polarized output light beams obtained from the polarizing beam splitter onto the respective entrances of the channels of the two-channel light-guiding device. The entrances can be arranged at a distance from the analysis device adapted to the physical conditions, and in any orientation with respect thereto. Adaptation to different measurement location sizes, and thus a high light yield, is additionally made possible.

In an alternative embodiment, the mirror objective is adjusted in such a way that it focuses at infinity, so that the return beam coming from the mirror objective is conveyed as an almost parallel light bundle to the polarizing beam splitter arranged between the mirror objective and the analysis device. By way of a lens arrangement placed after the polarizing beam splitter, the still-parallel light beam bundles of the s- and p-polarized output light beams obtained from the polarizing beam splitter are reduced in terms of their beam width so they can be coupled into the entrances of the measurement light guide channels.

In a preferred embodiment of the invention, the individual light-guiding fibers of the light-guiding devices are guided in bundled fashion as far as a coupling apparatus at an entrance of the analysis device, and there spread out. This allows a better separation of the signals from the individual light-guiding fibers to be achieved for subsequent analysis.

The arrangement of the ends of the individual light-guiding fibers can be grouped with respect to one another as necessary, for example by combining the light-guiding fibers of signals of different channels that correspond to one another; or the arrangement of the light-guiding fibers can be accomplished according to the corresponding points on the measurement location. Preferably the light-guiding fibers are sorted according to angle of incidence.

These groupings can be accomplished both mechanically, by combining the individual light fibers, and by way of a subsequent analysis of the arbitrarily spread-out light-guiding fibers by means of a software program, in which the experimentally ascertained positional relationships between the entrance side and exit side are programmed in individually for each light-guiding device.

In a preferred embodiment of the invention, however, the entrance ends and exit ends of the light-guiding fibers have the same positional relationship to one another for each of the light-guiding devices, so that for evaluation of the measurement result, the signals obtained from the different channels possess a similar information structure and thus can easily be compared to one another. If the light-guiding fiber ends that are adjacent at the entrance end are specifically arranged in adjacent formation at the exit end, signal influences between light-guiding fibers extending next to one another can be minimized.

The light-guiding fibers of the individual channels of the light-guiding devices are preferably spread out in a manner adapted to the analysis device used to examine the light, for example to a spectrograph having a slit-shaped entrance and a charge coupled device (CCD) detector for signal acquisition, and in particularly well-organized fashion in linear form.

In a further preferred embodiment, the entrance ends of the light-guiding fibers for each channel of the light-guiding devices are distributed over a surface that corresponds to an opening of an aperture stop within a measurement light beam emitted from the illumination source, the aperture stop being arranged before a beam splitter for splitting the measurement light beam into a component to be influenced by the specimen and a component that is not to be influenced by the specimen. This allows optimum utilization of the light-guiding fibers in the light-guiding devices, as well as a high light yield.

To optimize the light used for measurement, an illumination apparatus having a halogen lamp and a deuterium lamp is provided, the halogen lamp shining through an opening in the deuterium lamp. Also provided, between the illumination device and the aperture stop, is a lens arrangement which sharply images the filament of the halogen lamp in the aperture stop. This results in a homogeneous light-source volume with a broad spectral range from 190 nm to 800 nm that is continuously available for measurement purposes.

To define the specimen field size at the measurement location that is used during measurement, a pinhole mirror, through which the return beam coming from the mirror objective is guided, is provided between the mirror objective and the polarizing beam splitter. The pinhole can be provided, for example, on a semitransparent mirror with which a portion of the light of the return beam can be diverted to a CCD video camera so that a measurement process can be monitored and optionally recorded.

In a further embodiment, the measurement arrangement according to the present invention is equipped with a device for leveling, which is capable of ascertaining and correcting directional deviations between the line normal to the specimen surface and the angle bisector between the incident and return beams of the measurement arrangement. The manner of operation and configuration of such devices is known from the existing art and therefore will not be explained further here.

In the context of the two aforementioned alternative embodiments, an alignable quarter-wave plate of a common type, which allows the entire UV-VIS-IR spectral region to pass, is positioned either directly after the polarizer or directly before the polarizing beam splitter. This advantageously yields the possibility of better control of the polarization state of the light that is to be analyzed, so that a shorter measurement time and greater measurement accuracy can be obtained.

The further advantages of the arrangement according to the present invention substantially consist, in summary, in the fact that short measurement times and thus a higher throughput of, for example, wafers during production inspection can be achieved. In addition, a measurement accuracy of 0.1 nm or less is attained for layer thickness measurements. A substantial advantage is the fact that a complete spectrum in the UV-VIS-IR region can be recorded simultaneously over a wide angle of incidence, thus making possible a high lateral specimen resolution of between 400 nm and 2 μm.

The use of the mirror objective in conjunction with the ellipsometric measurement method allows measurement accuracies in the sub-nanometer range to be achieved with a simple, compact configuration, the incident beam being directed by way of the mirror objective onto the measurement location on the surface, and the return beam also being acquired by the mirror objective. This makes it possible to eliminate the separate optical assemblies used heretofore in the existing art for spectroscopic ellipsometry. This arrangement with a mirror objective can be used for spectroscopic as well as ellipsometric measurements, so that equipment outlay is reduced and a particularly space-saving design for the arrangement as a whole can be realized.

It is possible with this arrangement to determine reflection simultaneously for different stepper wavelengths, such as 193 nm, 250 nm, and 365 nm. Optical material properties, such as, for example, refractive index n and extinction factor can also be measured in time-effective fashion over the very wide UV-VIS-IR spectral region.

The specially configured four-armed light guide cross-section converter that is described herein makes a substantial contribution to achievement of the object of the invention.

BRIEF DESCRIPTION OF THE DRAWINGS

The invention will be explained in more detail below with reference to an exemplary embodiment depicted in the drawings, in which.

DETAILED DESCRIPTION OF THE INVENTION

The exemplary embodiment shows an optical measurement arrangement for layer thickness measurement that can be arranged, for example, in a continuous production line for wafer manufacture in order to inspect the surfaces of the wafers.

Figure 1:
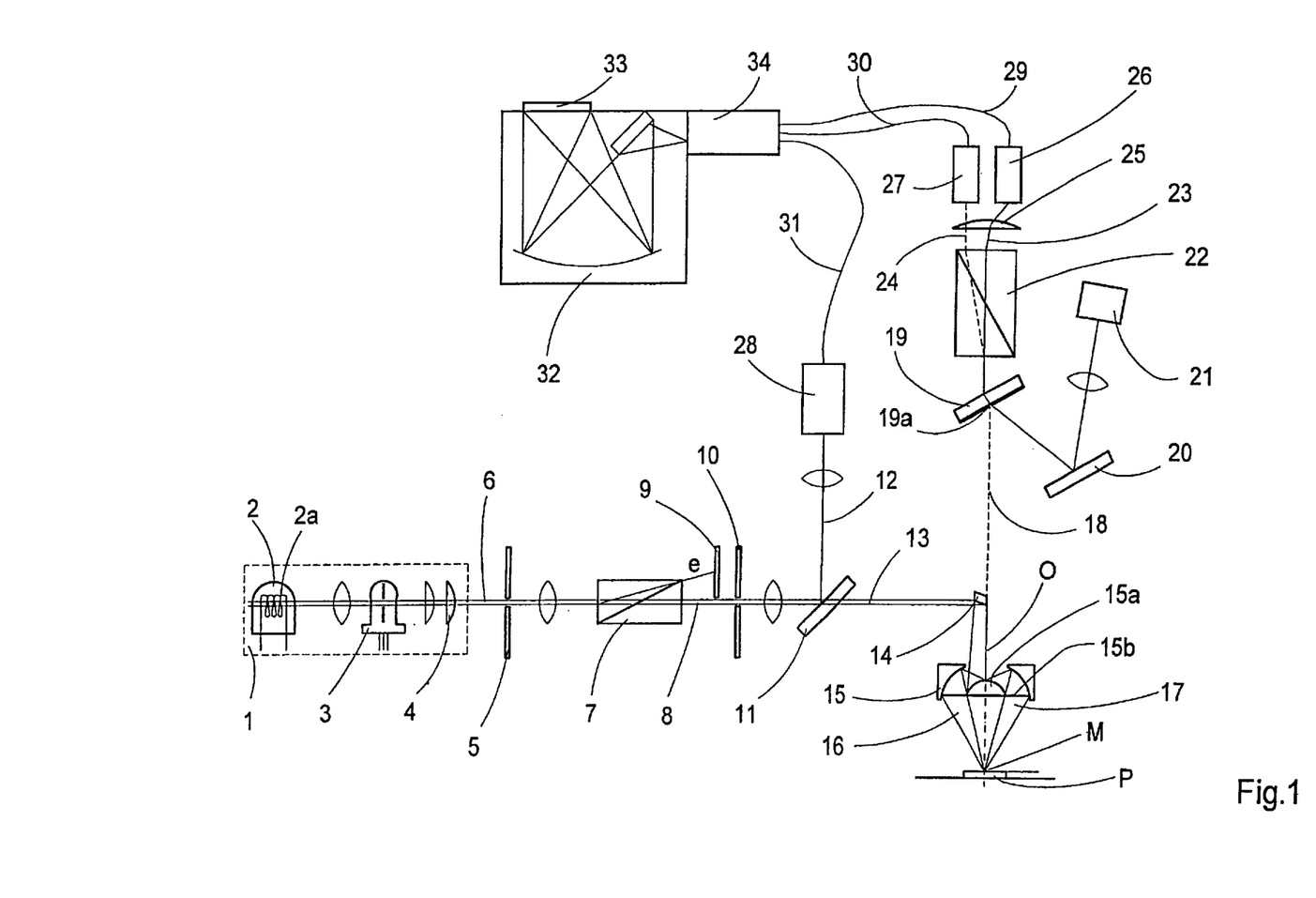
FIG. 1 shows an exemplary embodiment of an optical measurement arrangement for ellipsometry, which is used here for layer thickness measurement.

The measurement arrangement comprises firstly an illumination device 1 in which a measurement light beam 6 required for the measurement is generated. Illumination device 1 comprises a halogen lamp 2 that is filled, for example, with krypton. For particularly high light output, however, a xenon filling is preferred. A deuterium lamp 3, which serves as a UV-VIS light source, is additionally arranged between halogen lamp 2 and the exit of measurement light beam 6 from illumination device 1. To prevent large fluctuations in light intensity, deuterium lamp 3 has an internal deep-UV (DUV) filter which filters out light below a wavelength of 190 nm in order to prevent the creation of ozone. Lamps which do not have such a filter are unsuitable for investigations at short wavelengths, since light absorption by ozone in the light path at a wavelength of approximately λ=250 nm causes intensity fluctuations that are perceptible during measurement as a disturbing unsteadiness of the lamp.

Figure 4:
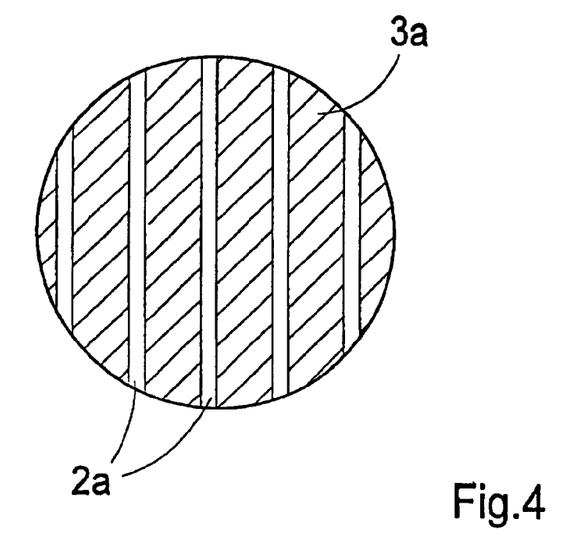
FIG. 4 shows a viewing opening of a deuterium lamp with the filament of a halogen lamp of an illumination device of the arrangement shown in FIG. 1.
Figure 5:
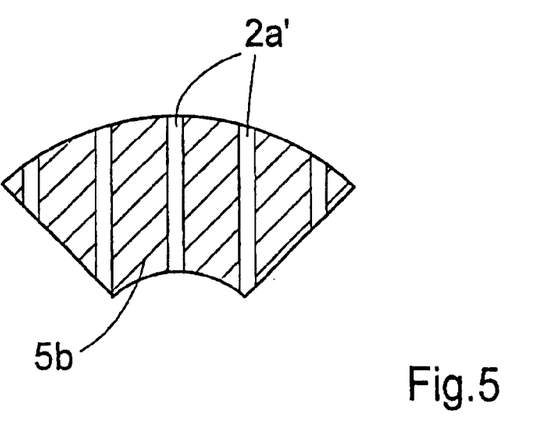
FIG. 5 shows the image of the filament of the halogen lamp in the opening of the aperture stop.

In the exemplary embodiment, deuterium lamp 3 is equipped with a viewing opening 3a that is depicted in FIG. 4. Viewing opening 3a, as well as the front side of a filament 2a of halogen lamp 2, are sharply imaged in the plane of an aperture stop 5 that is explained in further detail below. For that purpose, a suitable lens arrangement 4 is placed after halogen lamp 2 and deuterium lamp 3 in the direction in which light emerges from illumination device 1.

When a conventional deuterium lamp (not depicted in the drawings) without a viewing opening 3a is used, a hinged mirror is provided, with which light can be directed to aperture stop 5 alternatingly from a deuterium lamp or from a halogen lamp. This advantageously eliminates the $D_2$ red peak for VIS measurements.

The combined use of a deuterium lamp 3 with viewing opening 3a together with a halogen lamp 2, on the other hand, means that a measurement light in a wavelength region from 190 nm to 800 nm can be made continuously available, thus allowing a particularly simple illumination device 1 to be realized. In contrast to a hinged-mirror arrangement with which the light of the deuterium lamp or of the halogen lamp can be alternatingly switched in, the operation of switching over the hinged mirror is eliminated with the exemplary embodiment depicted here, thus promoting a higher specimen throughput through the measurement arrangement. In principle, however, it is also possible to direct light from two different sources onto aperture stop 5 via suitable stationary mirror arrangements.

Figure 2:
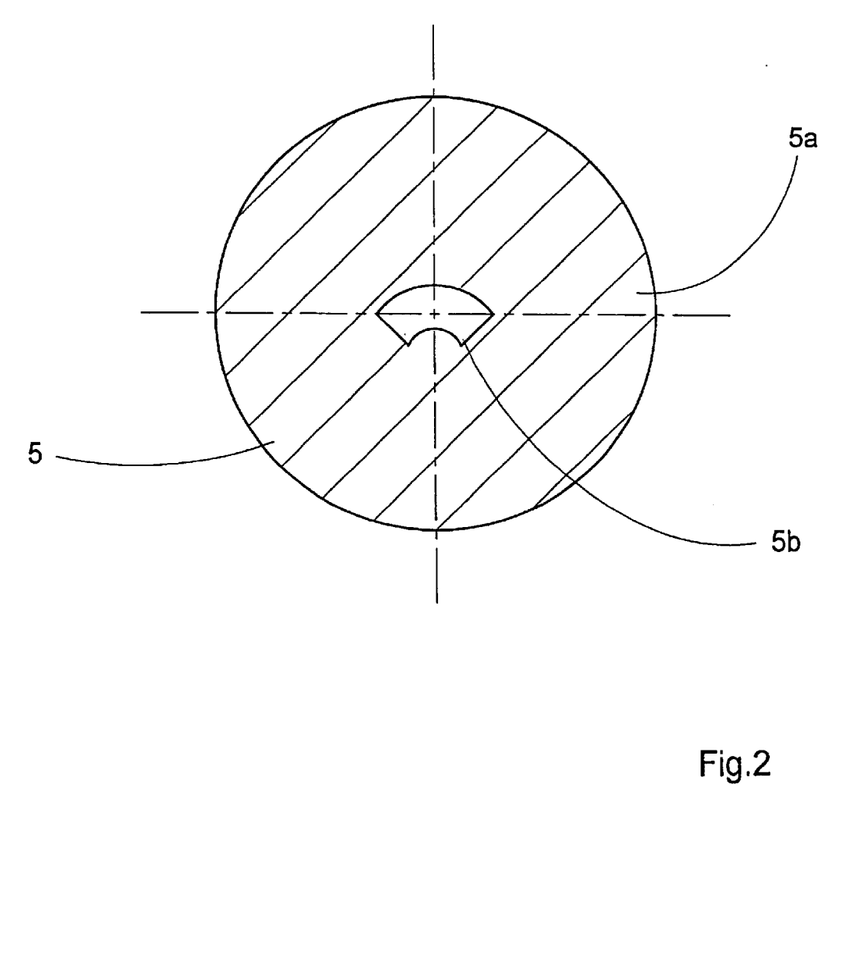
FIG. 2 shows a detail view of an aperture stop that is used in the measurement arrangement shown in FIG. 1.

Aperture stop 5, already mentioned, is depicted in detail in FIG. 2. It comprises firstly an opaque metal foil 5a in which a transparent, in particular glass-free, aperture opening 5b is configured. Opening 5b here takes the shape of a quarter of a circular ring, and thus corresponds to a quarter of the pupil opening of a measurement objective. A2

Measurement light beam 6 penetrating through aperture stop 5 strikes a polarizer 7 that is transparent in the UV, VIS, and NIR regions. In the exemplary embodiment depicted in FIG. 1, polarizer 7 is of the Rochon type, with which the arriving measurement light beam 6 is split into an ordinary beam of polarized light 8 that proceeds straight ahead, and an extraordinary beam of polarized light e that is deflected. The latter is blocked by a stop 9 placed after polarizer 7. Polarized beam 8 that proceeds straight ahead, on the other hand, passes through a field stop 10 and then encounters a beam splitter 11 in the form of a semitransparent deflection mirror with which the polarized light is split into a reference light beam 12 and a specimen light beam 13. The former is conveyed directly to an analysis device 33, whereas specimen light beam 13 is directed to a measurement location M on the surface of a specimen P, and after being influenced by the specimen is conveyed to analysis device 33.

As is evident from FIG. 1, specimen light beam 13 is switched via a half-mirror 14 into the entrance pupil of a mirror objective 15, and from there is directed as incident beam 16, over an angular range $\alpha_1$, $\alpha_2$ of approximately 18° to 41° with respect to the specimen surface, onto measurement location M.

For high measurement accuracy, it is necessary for the measurement light not to be degraded by edges or struts as it travels to measurement location M. On the other hand, a central mirror 15a provided in mirror objective 15 must be attached to a housing of mirror objective 15. This is preferably accomplished by way of strut-like retainers (a total of four struts 15b being provided here) which each extend between a primary mirror and the secondary mirror of mirror objective 15. Opening 5b of aperture stop 5 is selected and arranged in such a way that specimen light beam 13 is directed through between two adjacent struts 15b of mirror objective 15 without being influenced. If the number of struts 15b is different, the shape of opening 5b of aperture stop 5 must be correspondingly adapted so as to prevent any impairment of specimen light beam 13 by struts 15b.

Specimen light beam 13, as linearly polarized incident beam 16, is reflected from the surface of specimen P, the wave amplitude and phase of the polarization components of the light parallel and perpendicular to the plane of incidence being modified differently for different angles of incidence. From these changes, conclusions can be drawn, by calculation, as to the surface structure, layer thicknesses, and/or optical material properties at measurement location M. For that purpose, the reflected specimen light beam 13, as output beam 17, is captured by mirror objective 15 and conveyed by the latter, as output beam 18 under examination, by way of further optical assemblies to an analysis device 33.

Because of the quarter-pupil division in mirror objective 15, only half of a pupil opening is required, in total, for ellipsometry. The remaining portions can be used, for example, for an autofocus optical system (not depicted in the drawings) with which the distance from specimen P to mirror objective 15 can be set.

Figure 8:
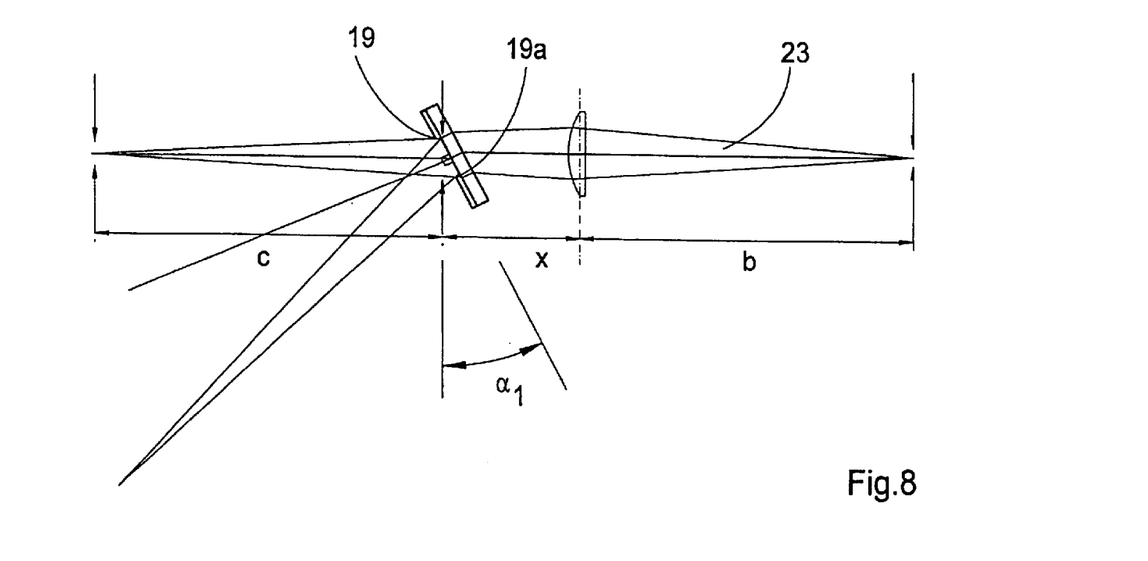
FIG. 8 shows a detail view of the arrangement of a pinhole mirror in the return beam between the mirror objective and the polarizing beam splitter.

Return beam 18 that emerges from the back side of mirror objective 15 and is to be examined passes through a pinhole mirror 19 and reaches a polarizing beam splitter 22, usually also referred to in the art as an "analyzer." The size of pinhole 19a defines the specimen field size used during measurement. Pinhole mirror 19 is of semitransparent configuration, so that at this point, after deflection by a further mirror arrangement 20, a portion of return beam 18 coming from mirror objective 15 can be conveyed to an examination or observation device or can be recorded by means of a CCD video camera 21.

In the exemplary embodiment depicted, polarizing beam splitter 22 is of the Wollaston type. With this, return beam 18 is split into two output light beams 23 and 24, one of which is s-polarized and the other p-polarized. In contrast to the Rochon prism that can also be used here, the Wollaston prism that is depicted yields a greater separation angle between the differently polarized output light beams 23 and 24.

By way of a converging lens 25 located after polarizing beam splitter 22, the two output light beams 23 and 24, having the pupil shape predefined by aperture stop 5, are focused respectively onto an entrance 26 and 27 of a two-channel light-guiding device for the reflected specimen light. Each measurement light guide 29 and 30 comprises a bundle of individual light-guiding fibers 26b and 27b respectively, which proceed to an optical coupling device 34 which is arranged in front of the entrance of an analysis device 33.

A reference light guide 31 having a plurality of light-guiding fibers 28b, which proceeds to coupling device 34, is also provided for reference light beam 12.

The arrangement of the individual light-guiding fibers 26b, 27b, and 28b is depicted, by way of example, with reference to channel KR of reference light guide 31. As is evident from FIG. 3, at channel entrance 28 the quarter-pupil shape of aperture stop 5 is imaged onto the cross-sectional surface of the ends of the bundle of light-guiding fibers 28b. When a measurement occurs, there is thus an unequivocal relationship between an individual light-guiding fiber and a specific angle of incidence and return angle at a measurement location M. The exit ends of the individual channels KS, KP, and KR are each spread out in linear form at coupling device 34, since a CCD detector is used as analysis device 33. The arrangement of the individual light-guiding fibers 26b through 28b is grouped in such a way that the light-guiding fibers correspond to a continuously increasing or a continuously decreasing angle of incidence at specimen P. This has the advantage that intensity fluctuations between adjacent light-guiding fibers of a channel turn out to be less than in the case of a random arrangement, thereby minimizing crosstalk effects between the adjacent light-guiding fibers. The grouping is effected in the same fashion for all channels KS, KP, and KR.

Figure 3:
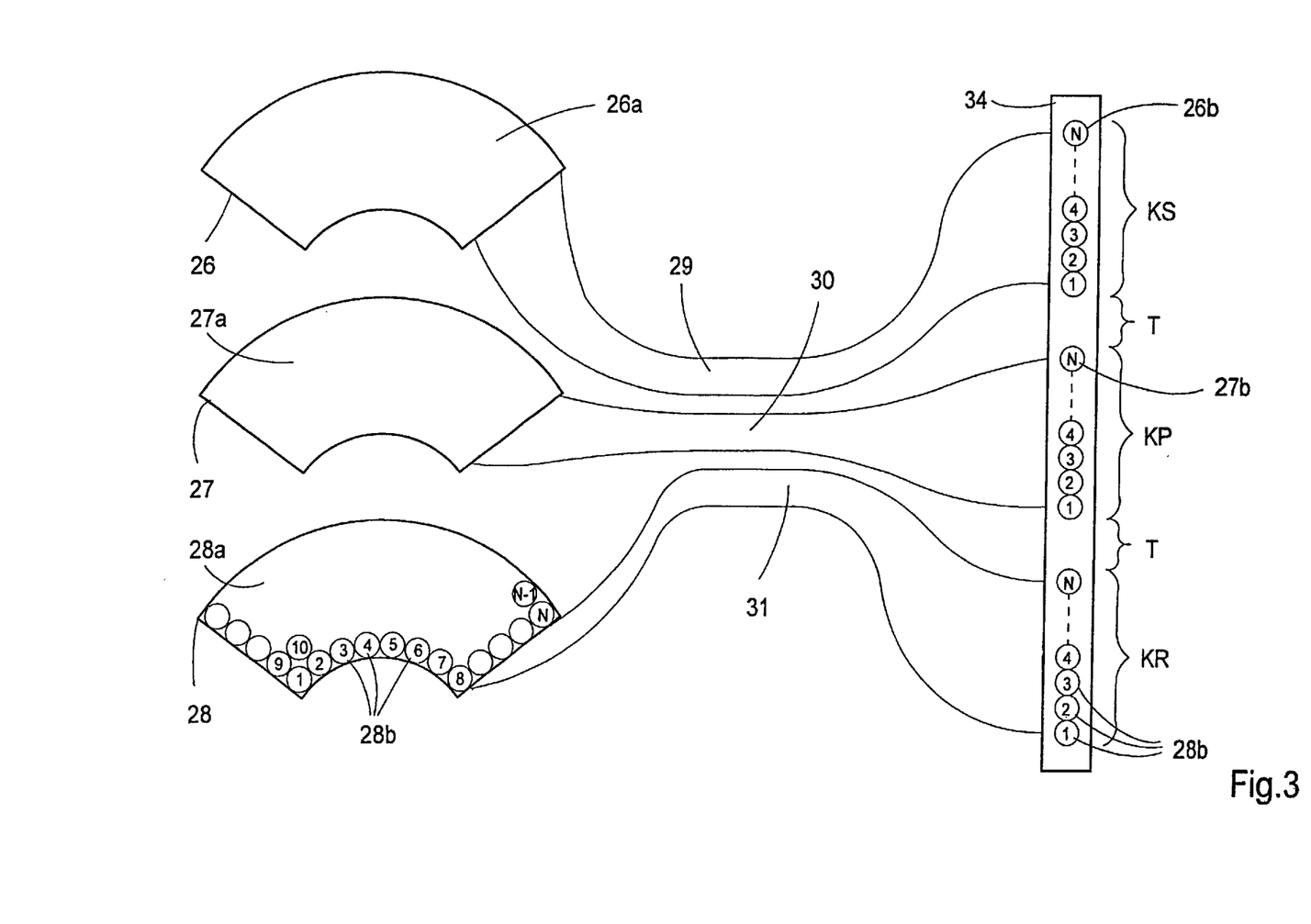
FIG. 3 shows a detail view of measurement light guides and reference light guides used in the arrangement shown in FIG. 1.

The light-guiding fiber ends can of course also be arranged with respect to one another at coupling device 34 in defined fashion in accordance with a different arrangement specification. For example, the light-guiding fibers of different channels KS, KP, and KR belonging to an identical angle of incidence can be collected into groups.

To differentiate between the individual channels KS, KP, and KR at analysis device 33, a separating distance T is provided in each case between them. The individual channels KS, KP, and KR are separated from one another by a distance T of, for example, 0.4 to 1 mm, the total length of the channels lined up one behind another being, for example, 6 mm.

Transfer of the output signals of coupling device 34 to the CCD detector of analysis device 33 is accomplished via a spectrograph 32. In the exemplary embodiment depicted, an imaging mirror-grating spectrograph having a two-dimensional CCD detector is used. This CCD detector is sensitive in the wavelength region from 190 nm to 800 nm. The use of a UV-sensitive, cooled CCD detector having a low dark current, illuminated from the back side, makes possible a rapid readout (within one second) of the measurement spectra.

With the optical measurement arrangement described above, both ellipsometric and spectroscopic investigations can be performed using the same mirror objective 15. The result is thus a simple and compact configuration for the measurement arrangement, in which the dual capability of the mirror objective moreover means that alignment complexity is also minimized.

Certain details of the imaging of return beam 18 onto entrances 26 and 27 of measurement light guides 29 and 30 will be further discussed below. The assemblies relevant in this context are depicted in FIG. 6, polarizing beam splitter 22 having been omitted.

Figure 6:
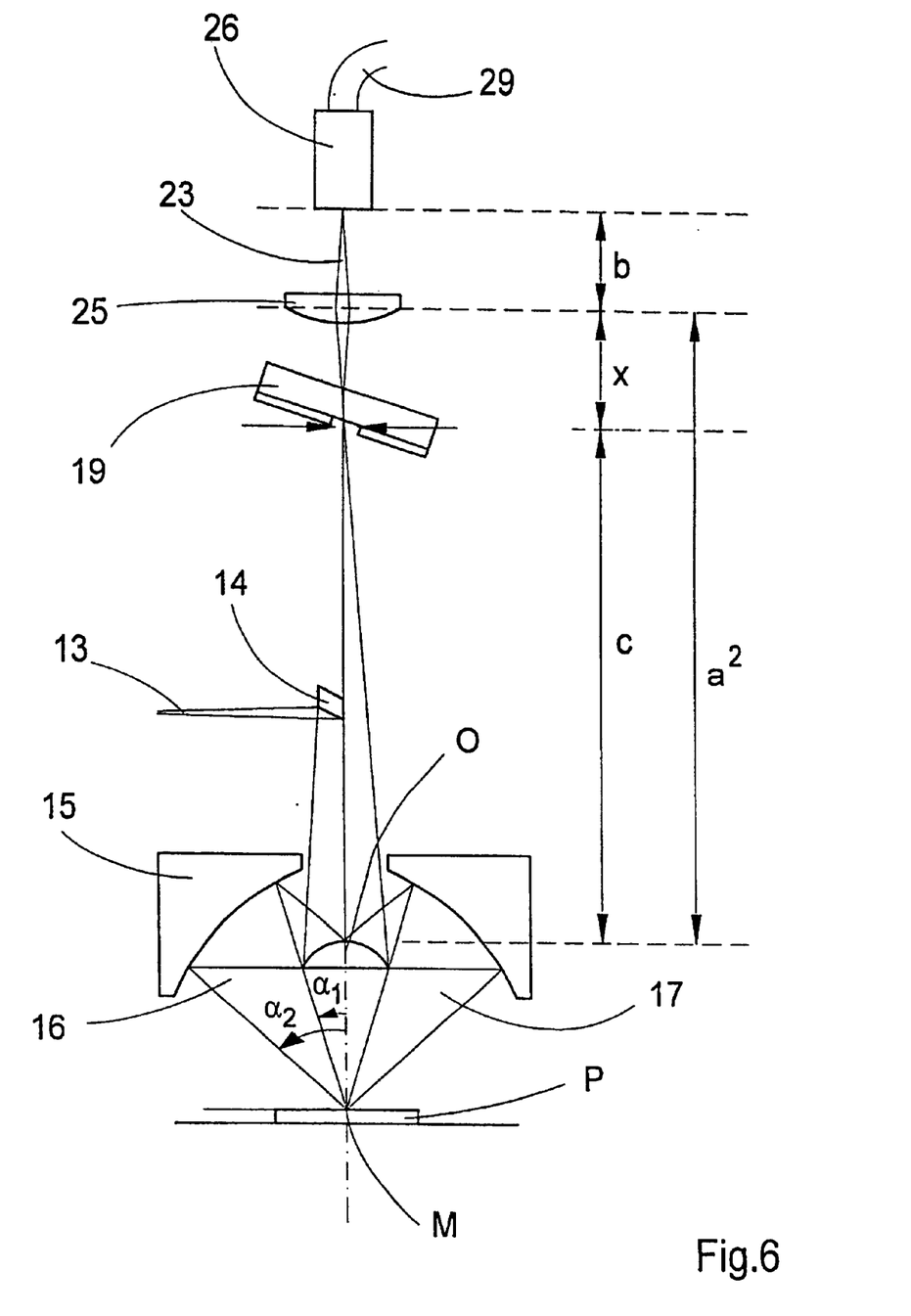
FIG. 6 schematically depicts a return beam from a measurement location on a specimen up to the point where it is coupled into a measurement light guide, a polarizing beam splitter additionally depicted in FIG. 1 here being omitted.
Figure 7:
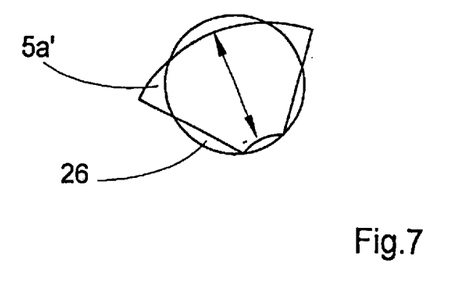
FIG. 7 shows the image of the aperture opening on a round entrance of a measurement light guide channel.

Mirror objective 15 depicted in FIG. 6 has a 74×magnification with a numerical aperture of 0.65. For a distance a=200.5 mm between the entrance pupil of mirror objective 15 and converging lens 25, and a distance b=107.5 mm between converging lens 25 and entrance 26 of measurement light guide 29, the result, with a converging lens 25 having a focal length f=70 mm, is that the entrance pupil of mirror objective 15 is reduced by a factor of 0.54. The distance between converging lens 25 and pinhole mirror 19 is 20 mm. A pupil having an outside diameter of 3.35 mm and an inside diameter of 1.5 mm can thus be imaged onto a radial width Δr of approximately 0.5 mm, as depicted in FIG. 7. In this, quarter-pupil 5a' is focused onto entrance 26 of measurement light guide 29 with a circular arrangement of the light-guiding fiber bundles, entrance 26 having a diameter of approximately 0.5 mm. The individual light-guiding fibers have a core diameter of approximately 50 μm to 150 μm. For example, light-guiding fibers having a core diameter of 80 μm can be used, so that there are approximately ten light-guiding fibers along the inner edge of the pupil.

Figure 9:
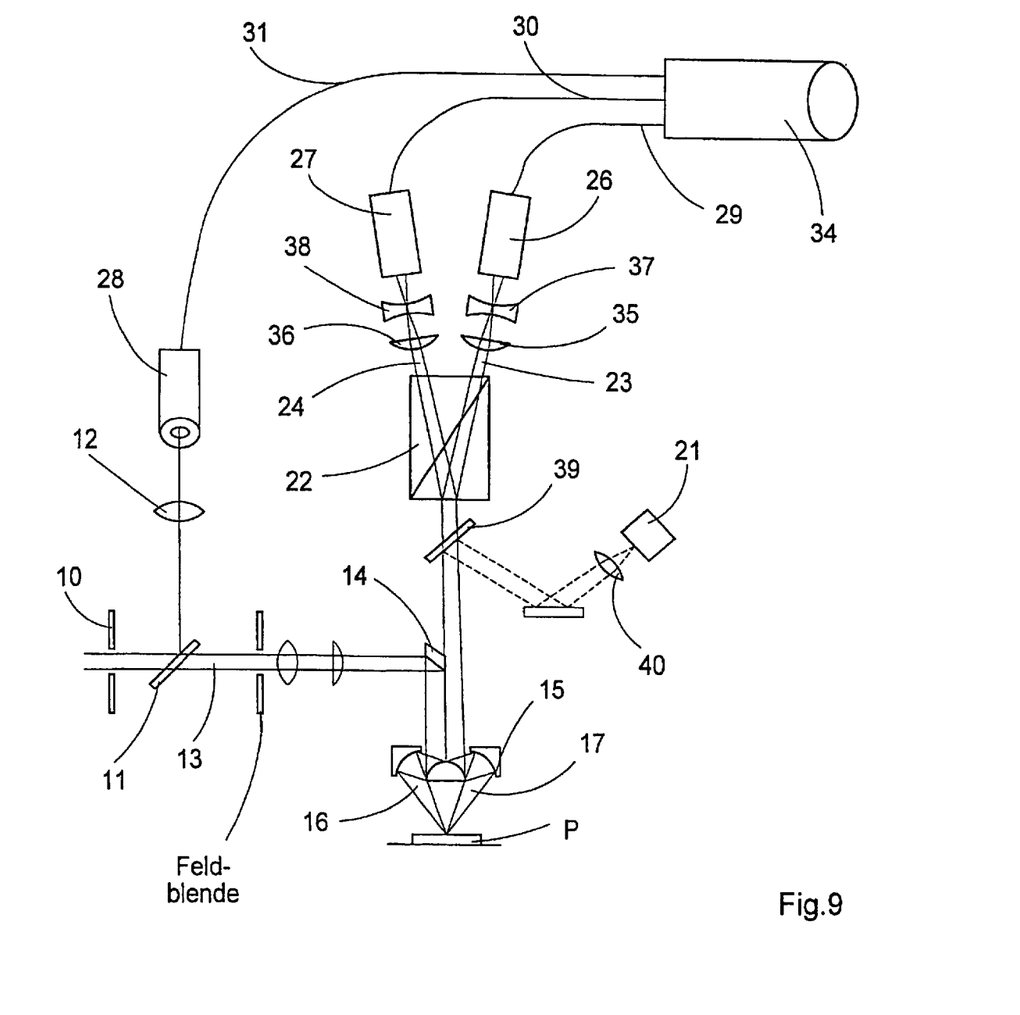
FIG. 9 shows a variant of the embodiment shown in FIG. 1, in which the return beam is introduced into the polarizing beam splitter as a parallel light bundle.

An alternative embodiment is depicted in FIG. 9 in order to utilize the high aperture of mirror objective 15 for a microspot at a measurement location M with a lateral resolution between approximately 400 nm and 2 μm. For this purpose, the primary and secondary mirrors of mirror objective 15 are adjusted in such a way that it focuses at infinity. Polarizing beam splitter 22 is thus located in an almost parallel light beam bundle of return beam 18, which is advantageous in terms of the beam path through polarizing beam splitter 22.

In order to reduce exit beams 23 and 24 of polarizing beam splitter 22 to a width suitable for entrances 26 and 27 of channels KS and KP of measurement light guides 29 and 30, a respective planoconvex lens 35, 36 and respective planoconcave lens 37, 38 are arranged one behind another, similarly to a reverse laser-beam expansion system, between polarizing beam splitter 22 and the respective entrances 26, 27. In order to allow return beam 18 coming from mirror objective 15 to be acquired by a video camera 21, in this variant a hinged mirror 39 and a further lens optical system 40 are provided.

| Parts List | |
|---|---|
| 1 | Illumination device |
| 2 | Halogen lamp |
| 2a | Filament |
| 3 | Deuterium lamp |
| 3a | Viewing opening |
| 4 | Lens arrangement |
| 5 | Aperture stop |
| 5a | Metal foil |
| 5b | Aperture opening |
| 6 | Measurement light beam |
| 7 | Polarizer |
| 8 | Polarized beam |
| 9 | Downstream stop |
| 10 | Field stop |
| 11 | Beam splitter |
| 12 | Reference light beam |
| 13 | Specimen light beam |
| 14 | Mirror |
| 15 | Mirror objective |
| 15a | Central mirror |
| 15b | Struts |
| 16 | Incident beam |
| 17 | Output beam |
| 18 | Output beam |
| 19 | Pinhole mirror |
| 19a | Pinhole |
| 20 | Mirror arrangement |
| 21 | Video camera |
| 22 | Polarizing beam splitter |
| 23, 24 | Output light beams |
| 25 | Converging lens |
| 26, 27, 28 | Entrance |
| 26b, 27b, 28b | Light-guiding fiber |
| 29, 30 | Measurement light guide |
| 31 | Reference light guide |
| 32 | Spectrograph |
| 33 | Analysis device |
| 34 | Coupling device |
| 35, 36 | Planoconvex lens |
| 37, 38 | Planoconcave lens |
| T | Separating distance |
| P | Specimen |
| M | Measurement location |
| KS, KP, KR | Channels |

What is claimed is:

1. An optical measurement arrangement comprising:
   an ellipsometer, in which an incident beam of polarized light is directed at an angle of incidence α≠0° onto a measurement location on a surface of a specimen, and information concerning properties of the specimen is obtained from an analysis of a return beam reflected from the specimen;
   a mirror objective through which the incident beam is directed onto the surface of the specimen, wherein the return beam is also captured by the mirror objective;
   measurement light guides, which comprise a plurality of light-guiding fibers, configured to couple the light reflected from the specimen into an analysis device; and
   a reference light guide, which comprises a plurality of light-guiding fibers, configured to convey measurement light that is uninfluenced by the specimen to the analysis device,
   wherein the measurement light guides have channels KS, KP corresponding to s- and p-polarized components of reflected output beams, respectively, and the reference light guide has a channel KR, and wherein entrance ends of the individual light-guiding fibers for each channel KS, KP, KR are distributed over a surface that reproduces the shape of an opening of an aperture stop, said aperture stop arranged before the mirror objective to pass a measurement light beam to the mirror objective.

2. The optical measurement arrangement as defined in claim 1, wherein the incident beam strikes the measurement location within an angular range of approximately 18° to 41° from the optical axis of the mirror objective.

3. The optical measurement arrangement as defined in claim 1, wherein the individual light-guiding fibers of the measurement light guides and of the reference light guide are guided in bundled fashion to a coupling device, located at an entrance of the analysis device, and are spread out at the coupling device.

4. The optical measurement arrangement as defined in claim 3, wherein the individual light-guiding fibers of the channels KP, KS, and KR are each spread out in a linear arrangement.

5. The optical measurement arrangement as defined in claim 3, wherein, for each of the measurement light guides and the reference light guide, entrance ends of the individual light-guiding fibers and exit ends of the individual light-guiding fibers have the same positional relationship to one another.

6. The optical measurement arrangement as defined in claim 1, wherein the aperture stop is arranged before a beam splitter, the beam splitter configured to split the measurement light beam into a component to be influenced by the specimen and a component that is not to be influenced by the specimen.

7. The optical measurement arrangement as defined in claim 6, further comprising an illumination source having a halogen lamp and a deuterium lamp, a filament of the halogen lamp shining through a viewing opening of the deuterium lamp, and wherein the optical measurement arrangement further comprises a lens arrangement configured to sharply image the filament of the halogen lamp in the opening of the aperture stop.

8. The optical measurement arrangement as defined in claim 1, further comprising a polarizing beam splitter arranged after the mirror objective and configured so that the return beam coming from the mirror objective is divided, after passing through the polarizing beam splitter, into the s- and p-polarized reflected output beams.

9. The optical measurement arrangement as defined in claim 8, further comprising: a focusing lens arranged between the polarizing beam splitter and the measurement light guides, configured to focus the s- and p-polarized reflected output beams onto respective entrances of the measurement light guides.

10. The optical measurement arrangement as defined in claim 8, wherein the mirror objective is focused at infinity, so that the return beam coming from the mirror objective strikes the polarizing beam splitter arranged between the mirror objective and the analysis device as a parallel beam bundle.

11. The optical measurement arrangement as defined in claim 10, further comprising: a lens arrangement arranged between the polarizing beam splitter and the measurement light guides, configured to reduce the beam width of the still-parallel light beam bundles of the s- and p-polarized reflected output beams obtained from the polarizing beam splitter.

12. The optical measurement arrangement as defined in claim 8, further comprising a pinhole mirror arranged between the mirror objective and the polarizing beam splitter.

13. The optical measurement arrangement as defined in claim 1, wherein the information concerning properties of the specimen comprises one of layer thicknesses and optical material properties.

* * * * *